(12) United States Patent
Busnaina et al.

(10) Patent No.: US 9,518,950 B2
(45) Date of Patent: Dec. 13, 2016

(54) CHEMICAL SENSOR BASED ON HIGHLY ORGANIZED SINGLE WALLED CARBON NANOTUBE NETWORKS

(75) Inventors: Ahmed Busnaina, Needham, MA (US); Yung Joon Jung, Lexington, MA (US); Sivasubramanian Somu, Natick, MA (US); Aniket Datar, Marlborough, MA (US); Young Lae Kim, Stoneham, MA (US)

(73) Assignee: Northeastern University, Boston, MA (US)

( * ) Notice: Subject to any disclaimer, the term of this patent is extended or adjusted under 35 U.S.C. 154(b) by 349 days.

(21) Appl. No.: 14/239,664

(22) PCT Filed: Aug. 20, 2012

(86) PCT No.: PCT/US2012/051592
§ 371 (c)(1),
(2), (4) Date: Feb. 19, 2014

(87) PCT Pub. No.: WO2013/081684
PCT Pub. Date: Jun. 6, 2013

(65) Prior Publication Data
US 2014/0197046 A1    Jul. 17, 2014

Related U.S. Application Data

(60) Provisional application No. 61/525,389, filed on Aug. 19, 2011.

(51) Int. Cl.
*G01N 27/414* (2006.01)
*B82Y 30/00* (2011.01)
(Continued)

(52) U.S. Cl.
CPC ............... *G01N 27/26* (2013.01); *B82Y 15/00* (2013.01); *B82Y 30/00* (2013.01); *G01N 27/127* (2013.01);
(Continued)

(58) Field of Classification Search
None
See application file for complete search history.

(56) References Cited

U.S. PATENT DOCUMENTS

2005/0129573 A1    6/2005  Gabriel et al.
2006/0055392 A1    3/2006  Passmore et al.
(Continued)

FOREIGN PATENT DOCUMENTS

EP        1895294        3/2008
WO    WO 2011/055298    5/2011

OTHER PUBLICATIONS

Nosrat Izadi, et al., "Hydrogen Sulfide Sensing Properties of Multi Walled Carbon Nanotubes", Ceramics International, vol. 38, No. 1, Jun. 24, 2011, pp. 65-75.
(Continued)

*Primary Examiner* — Neil N Turk
(74) *Attorney, Agent, or Firm* — Posternak Blankstein & Lund LLP

(57) ABSTRACT

A carbon nanotube-based micron scale chemical sensor or sensor array is provided that enables the remote detection of hydrogen sulfide and other chemicals in a gas stream. The sensor is suitable for use in harsh environments of high temperature and pressure such as those encountered during petrochemical exploration and recovery. Multiplex sensor devices detect two or more chemical agents simultaneously, or they can detect conditions such as pressure, salinity, humidity, pH, or scale-forming ions. Incorporation of read out electronics and an RF signal generator into the sensor (Continued)

device enables it to communicate to a relay station or receiver for 3D mapping or other analysis. Methods are also provided for fabricating the chemical sensor device and using the device for detection.

21 Claims, 15 Drawing Sheets

(51) Int. Cl.
- *B82Y 15/00* (2011.01)
- *G01N 27/26* (2006.01)
- *G01N 27/12* (2006.01)
- *G01N 33/00* (2006.01)
- *H01L 51/00* (2006.01)
- *H01L 51/05* (2006.01)
- *G01N 21/75* (2006.01)
- *G01N 21/77* (2006.01)

(52) U.S. Cl.
CPC ........ *G01N 27/414* (2013.01); *G01N 27/4146* (2013.01); *G01N 33/0044* (2013.01); *H01L 51/0048* (2013.01); *H01L 51/0049* (2013.01); *H01L 51/0575* (2013.01); *G01N 21/75* (2013.01); *G01N 21/77* (2013.01)

(56) References Cited

U.S. PATENT DOCUMENTS

| | | |
|---|---|---|
| 2006/0263255 A1 | 11/2006 | Han et al. |
| 2007/0114138 A1 | 5/2007 | Krasteva et al. |
| 2007/0196428 A1 | 8/2007 | Glauser et al. |
| 2008/0187604 A1* | 8/2008 | Tomaselli ............ A61K 9/0095 424/682 |
| 2009/0101501 A1 | 4/2009 | Tao et al. |
| 2009/0178921 A1 | 7/2009 | Lawrence et al. |
| 2010/0022045 A1 | 1/2010 | Segal et al. |
| 2010/0089772 A1 | 4/2010 | Deshusses et al. |
| 2010/0180667 A1 | 7/2010 | Bender et al. |
| 2010/0183844 A1 | 7/2010 | Xiong et al. |

OTHER PUBLICATIONS

Elena Bekyarova, et al., "Mechanism of Ammonia Detection by Chemically Functionalized Single-Walled Carbon nanotubes: In Situ Electrical and Optical Study of Gas Analyte Detection", Journal of the American Chemical Society, vol. 129, No. 35, Aug. 15, 2007, pp. 10700-10706.

* cited by examiner

CHEMICAL SENSOR BASED ON HIGHLY ORGANIZED SINGLE WALLED CARBON NANOTUBE NETWORKS

CROSS REFERENCE TO RELATED APPLICATIONS

This application claims the priority of U.S. Provisional Application No. 61/525,389 filed Aug. 19, 2011 and entitled "Chemical Sensor Based on Highly Organized Single Walled Carbon Nanotube Networks", the whole of which is hereby incorporated by reference.

BACKGROUND

Hydrogen sulfide ($H_2S$) is a deadly gas that causes asphyxiation, lung damage, and teratogenic effects when humans or animals are exposed to it (1-2). $H_2S$ gas is encountered widely in sources such as natural gas and petroleum, in mines, and as a by-product in the manufacture of rayon, synthetic rubber, and dyes, as well as in the tanning of leather (3-4). Thus, the monitoring and elimination of hydrogen sulfide is very important for safety. Up to now, a variety of inorganic and organic materials, such as tungsten oxide, tin oxide, and carbon have been proposed as electrical sensors that can detect $H_2S$ gas (5-11). Drawbacks of existing $H_2S$ monitors include high power consumption, high required operating temperatures, short lifetime, interference from other gases, and high cost (12). Many other chemical agents are encountered during petroleum extraction or mining operations that are either dangerous or corrosive, and whose detection by chemical sensors is desirable.

There has been significant interest in using carbon-based nanomaterials as chemical sensors due to advantages such as light weight, high electrical conductivity, high electrochemical surface area, and superior sensing performance. Carbon nanotubes (CNT), including single-walled carbon nanotubes (SWCNT), are particularly attractive due to their high electron mobility and large current carrying capacity. CNT can reduce power consumption and exhibit high temperature stability and chemical inertness, providing a stable and robust platform to detect specific analytes, such as gases (13-20). Chemical sensors containing untreated CNTs utilize their intrinsic electrochemical properties, which limits the sensor selectivity and sensitivity. One approach has been to functionalize CNTs either covalently or non-covalently with various materials (21-24). However, owing to their one-dimensional nanostructure, CNTs are highly sensitive to environmental factors such as humidity and temperature (25-26), which can restrict their use depending on the season, region, and weather. Thus, there is a need for more selective, specific, and stable nanoscale and microscale chemical sensor devices and methods for making and using them.

SUMMARY OF THE INVENTION

The invention provides microscale sensors for specifically detecting a chemical agent, methods for making the sensors, and methods of using the sensors to detect a chemical agent. The sensors and methods are well suited for use in harsh environments such as those encountered during petrochemical extraction. A "microscale" sensor as used herein refers to a sensor whose largest dimension or whose diameter is in the range of less than 1000 microns, or in certain embodiments less than 200 microns, less than 100 microns, less than 50 microns, less than 20 microns, or even less than 10 microns. Certain embodiments of the invention can be in the nanoscale range, less than 1 micron in size. The sensors are capable of detecting and quantifying chemical agents, such as hydrogen sulfide, at concentrations as low as 1 ppm or even in the ppb range (less than 1 ppm), and up to several hundred ppm, such as up to 100 ppm, 200 ppm, 300 ppm, or even 500 ppm. The sensors of the invention are capable of specific detection of chemical agents, such that their exposure to other chemical agents produces a signal of only 20% or less, 10% or less, or 5% or less, or even 1% or less than that of the specifically detected chemical agent.

One aspect of the invention is a microscale sensor for detecting a chemical agent. The sensor includes a substrate, a conductive layer attached to a surface of the substrate and forming at least one pair of electrodes with an insulating gap between the electrodes, and a conductive bridge consisting essentially of one or more functionalized single-walled carbon nanotubes bridging the gap between the electrodes. The one or more nanotubes are functionalized with a functional group that reacts with the chemical agent, which alters (increases or decreases) the conductivity of the bridge in a time-dependent manner. The amount of the chemical agent is generally proportional to the maximum (saturation level) conductance change.

Another aspect of the invention is a method of fabricating the chemical sensor just described. The method includes the steps of: (a) providing a substrate comprising a pair of conductive electrodes on a surface of the substrate, the electrodes configured so as to form a non-conductive gap between the electrodes; and (b) depositing a conductive bridge consisting essentially of one or more single-walled carbon nanotubes onto the substrate to span the gap between the electrodes and form an electrically conductive junction with each of the electrodes.

Yet another aspect of the invention is a method of detecting a chemical agent in a sample. The method includes the steps of: (a) measuring a baseline conductance value of the conductive bridge of the sensor described above in the absence of the sample; (b) exposing the conductive bridge to the sample; and (c) measuring a change in the conductance of the bridge in the presence of the sample compared to the absence of the sample, wherein the change in conductance indicates the presence or absence of the chemical agent in the sample.

Figure 3:
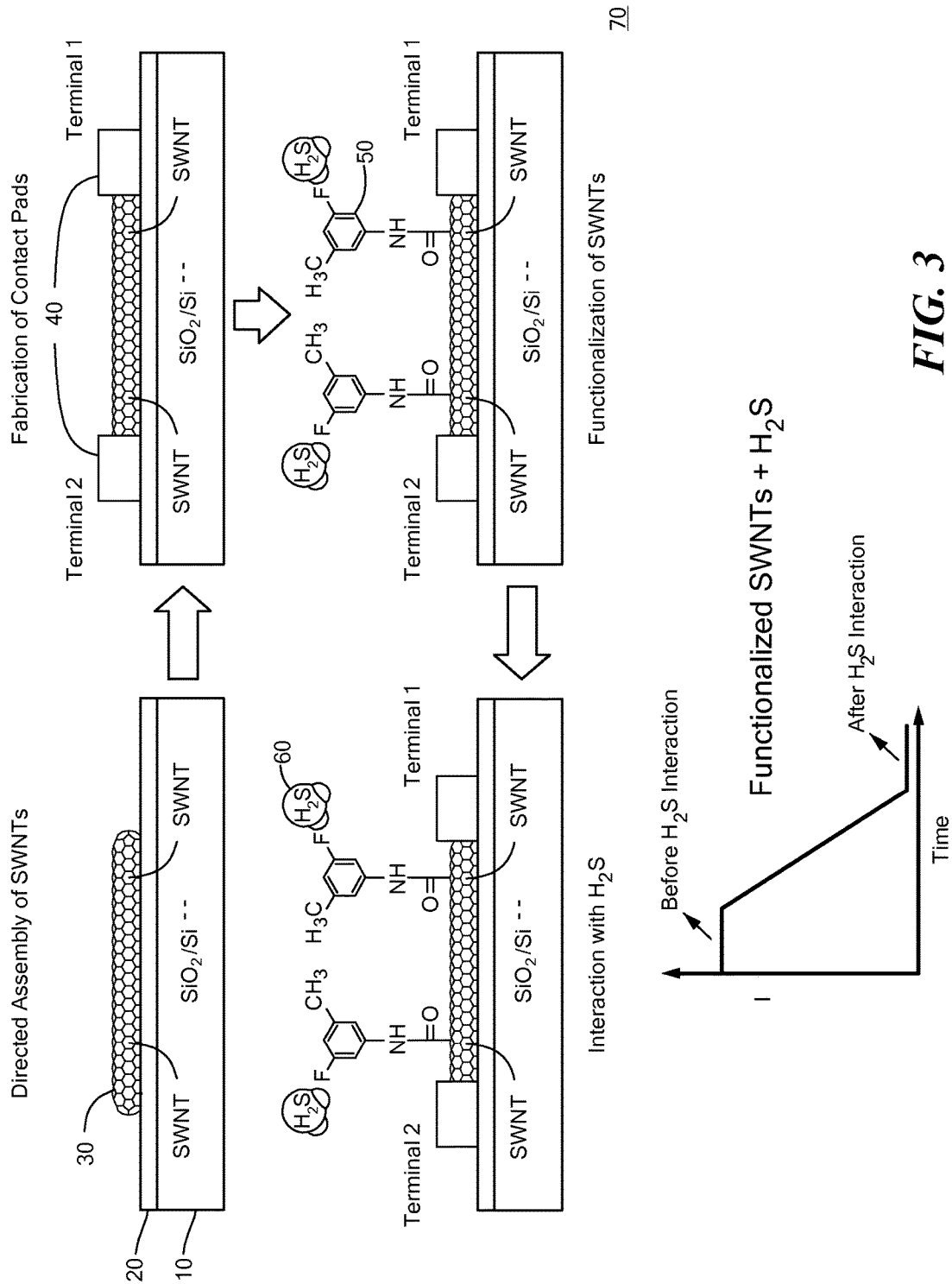

The upper portion of FIG. 3 shows a schematic diagram of a fabrication process for a chemical sensor device of the invention. The lower portion of FIG 3. shows a graph of the effect of $H_2S$ on current output of the sensor device.

Figure 4:
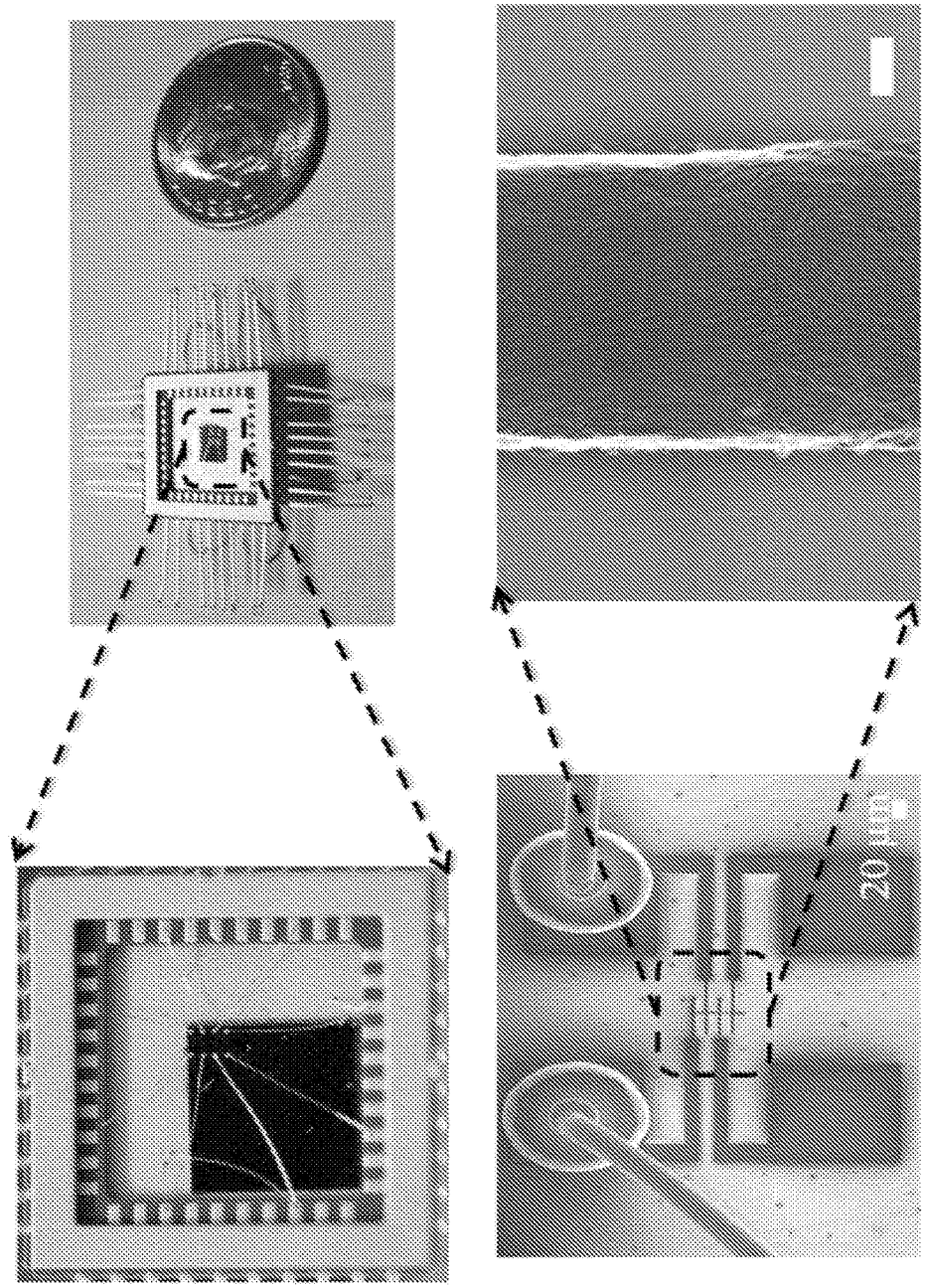

FIG. 4 shows a sensor device of the invention. The panel at the top shows optical images of the sensor device wire-bonded to a chip holder (top left) and the wire bonded chip compared to a U.S. dime for scale (top right). The lower panel shows a top viewed scanning electron micrograph (SEM) of the device (lower left) and of a single SWCNT channel (lower right).

Figure 5:
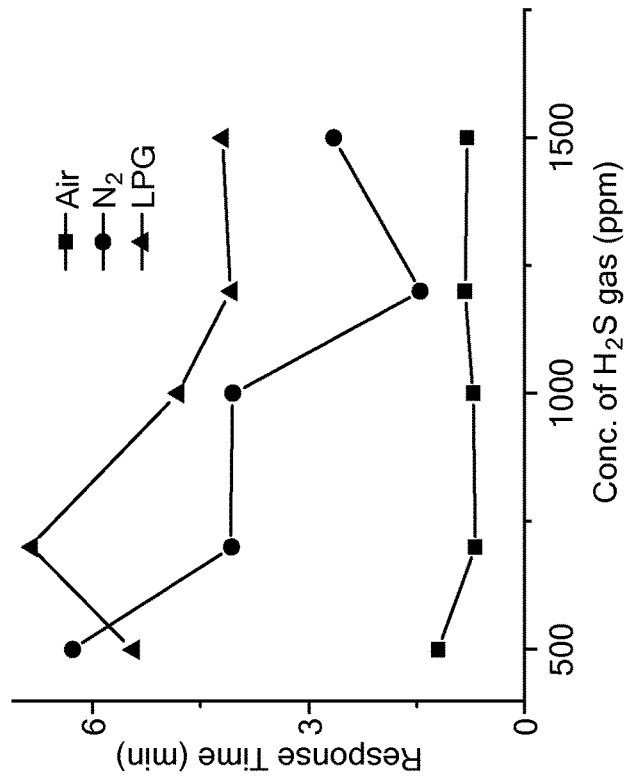
Figure 5:
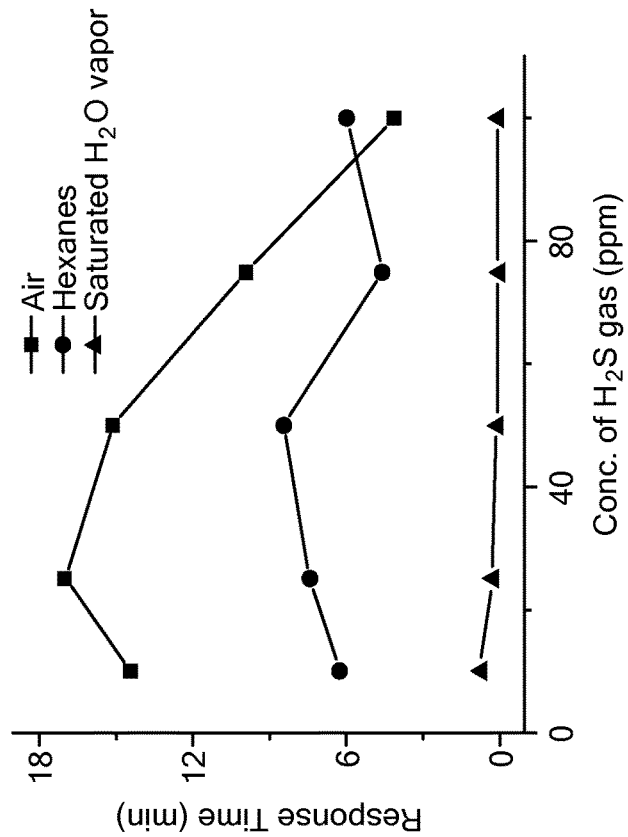

FIG. 5 shows the response time for various concentrations of $H_2S$ in air, hexanes and saturated water vapor (left panel) and for a higher range of $H_2S$ in air, nitrogen and LPG environments (right panel).

Figure 6A:
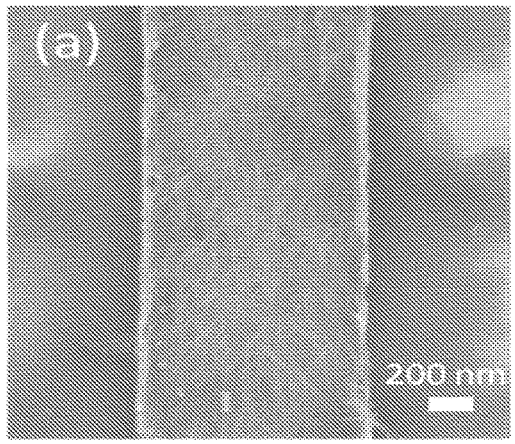
Figure 6B:
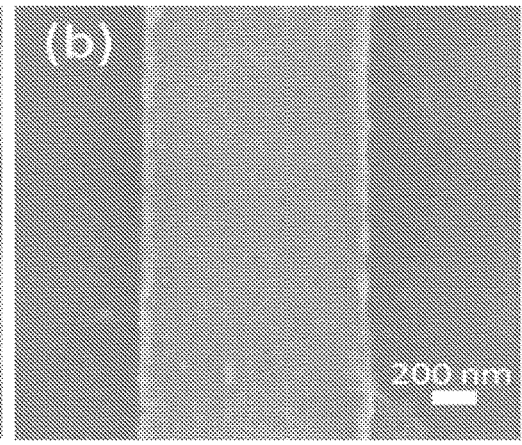
Figure 6C:
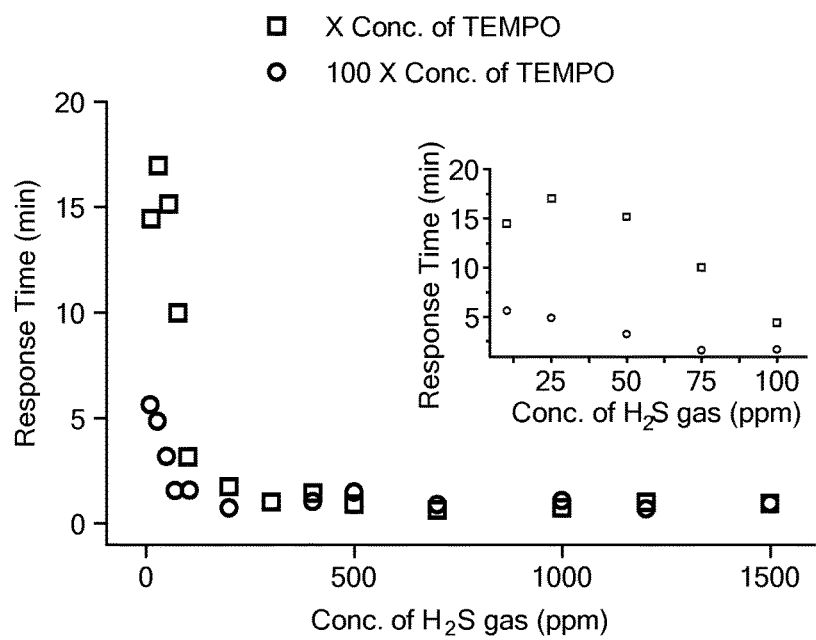

FIG. 6 shows an SWCNT channel with low functionalization (FIG. 6A) and an SWCNT channel with functionalization 100 times higher (FIG. 6B). FIG. 6C is a plot of response time as a function of concentration of $H_2S$. The inset shows the response time at the low range of concentration.

Figure 7:
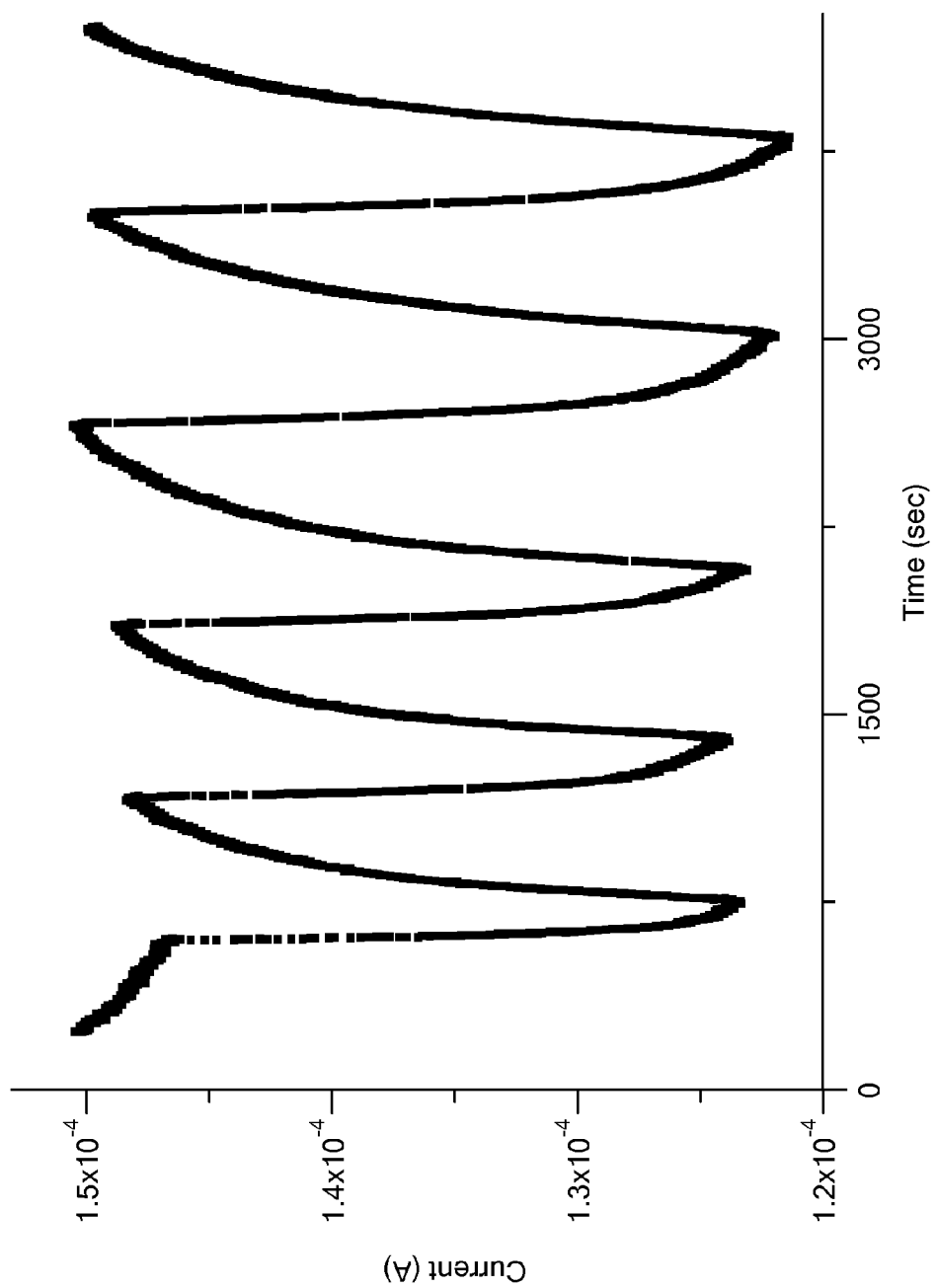

FIG. 7 shows the current flowing through a sensor device as function of time. The reduction in current was observed when $H_2S$ gas at 5 ppm concentration was injected and reached a plateau, while the current increased when the devices was exposed to atmospheric air.

Figure 8A:
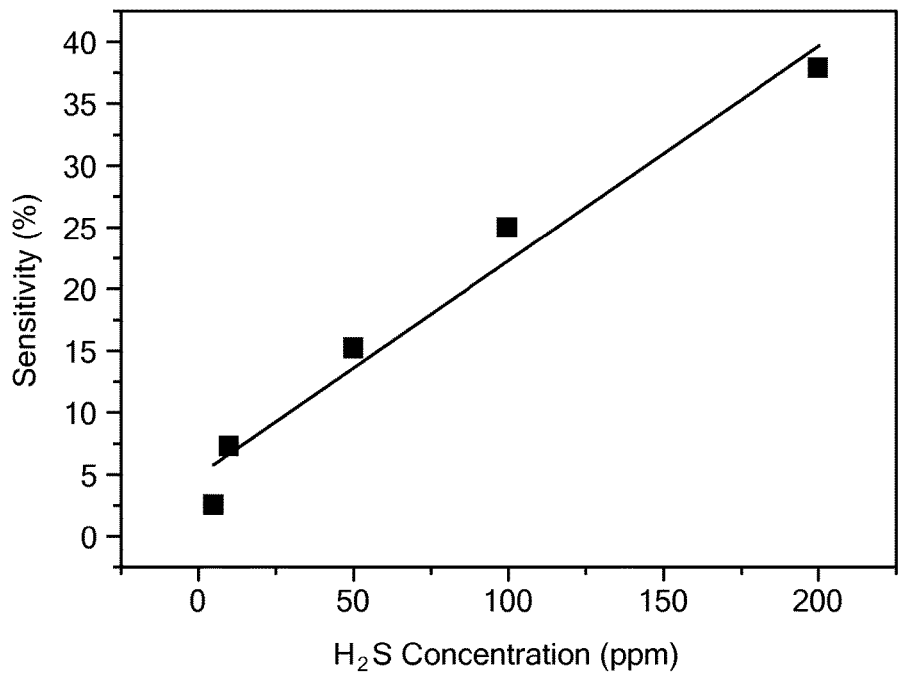
Figure 8B:
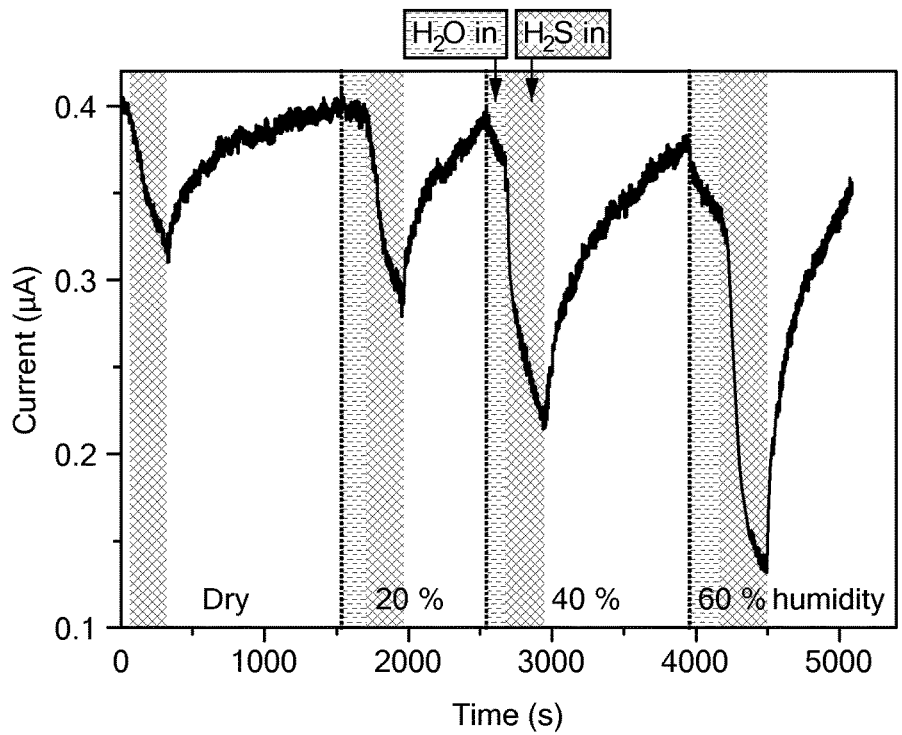
Figure 8C:
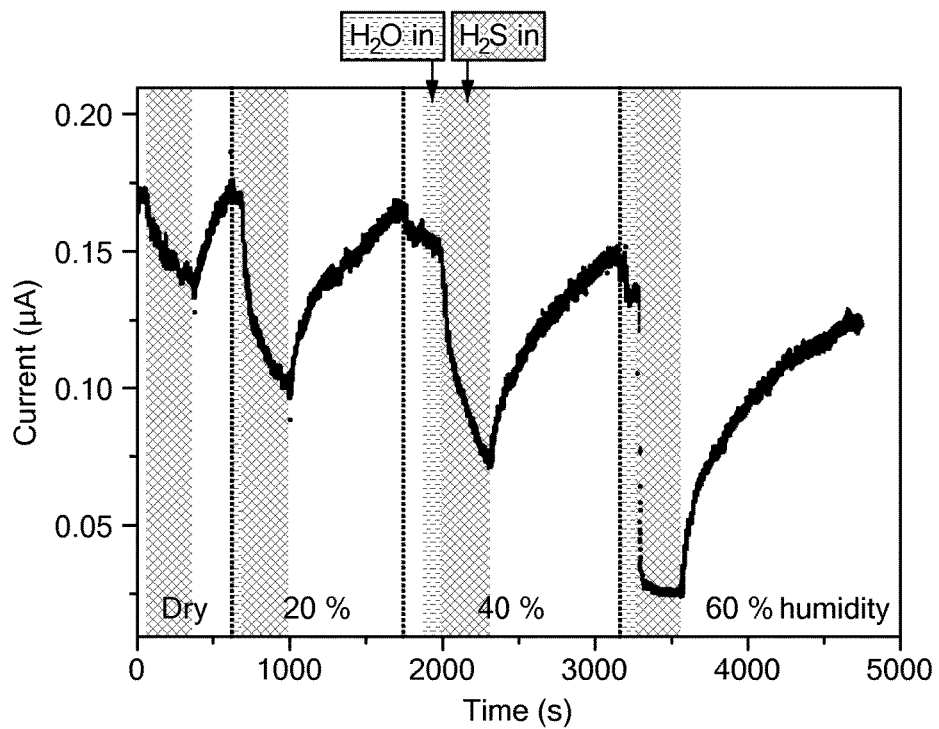
Figure 8D:
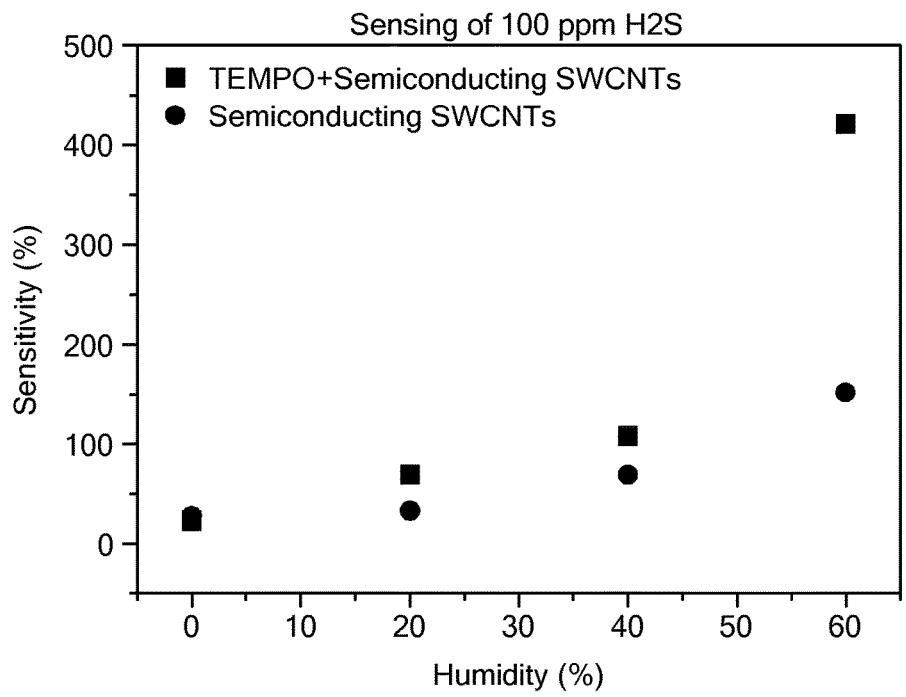

FIG. 8A shows the sensitivity of a bare (non-functionalized) s-SWCNT device as a function of $H_2S$ concentration. FIG. 8B shows a real-time current measurement of a bare s-SWCNT device as a function of relative humidity. FIG. 8C shows a real-time current measurement of a device containing s-SWCNT that have been functionalized with TEMPO as a function of relative humidity. FIG. 8D shows the sensitivity from FIGS. 8B and 8C as a function of relative humidity.

Figure 9A:
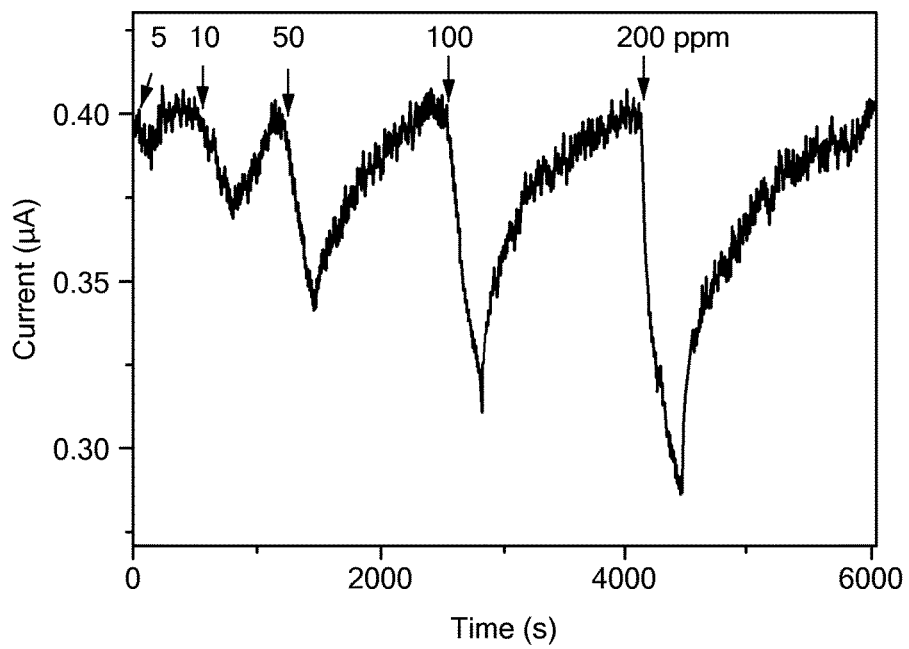
Figure 9B:
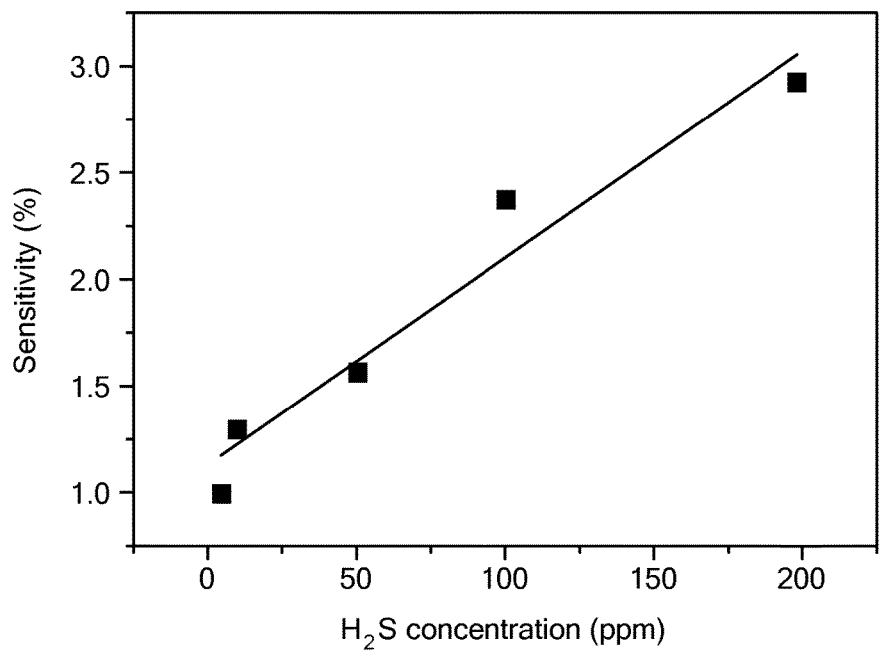

FIG. 9A shows real time current changes of a bare (non-functionalized) s-SWCNT device exposed to $H_2S$ gas at concentrations of 5, 10, 50, 100, and 200 ppm in dry $N_2$. FIG. 9B shows the sensitivity of a bare (non-functionalized) m-SWCNT device as a function of the $H_2S$ concentration in dry $N_2$.

Figure 10A:
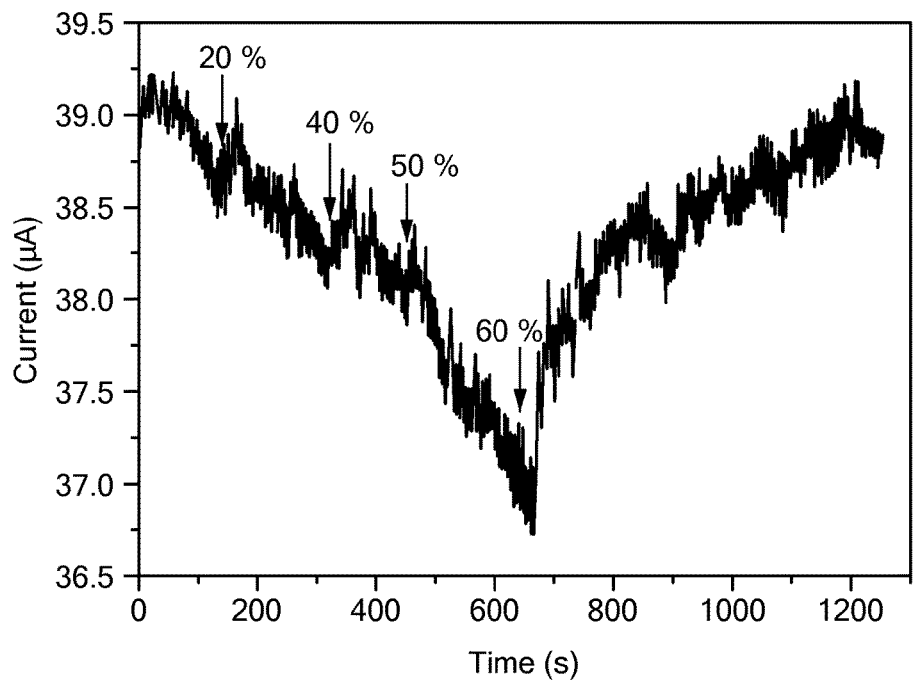
Figure 10B:
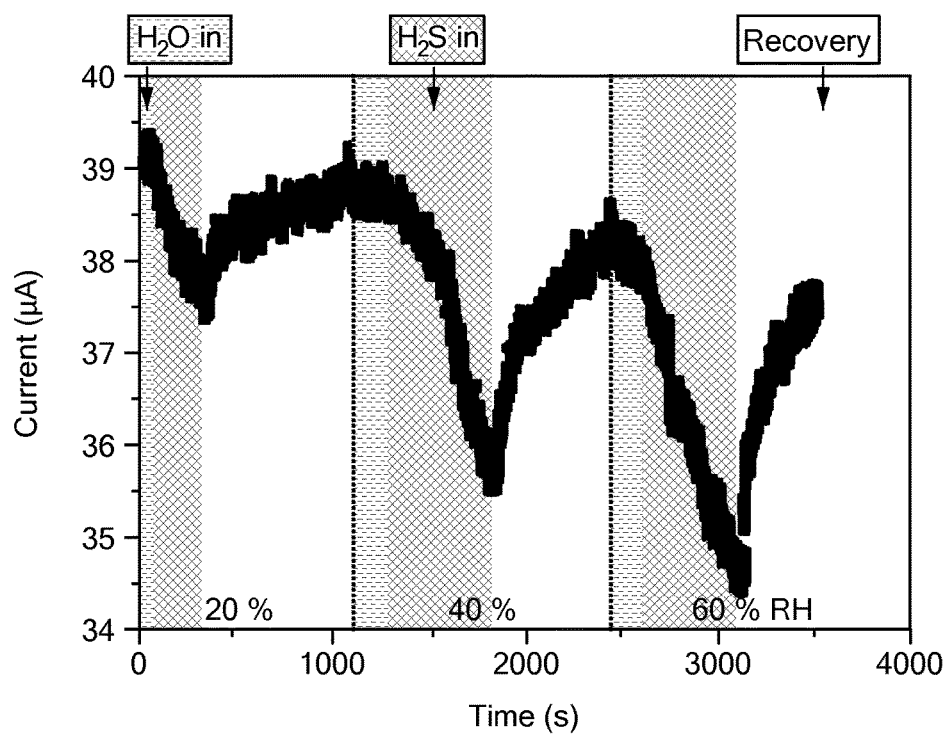
Figure 10C:
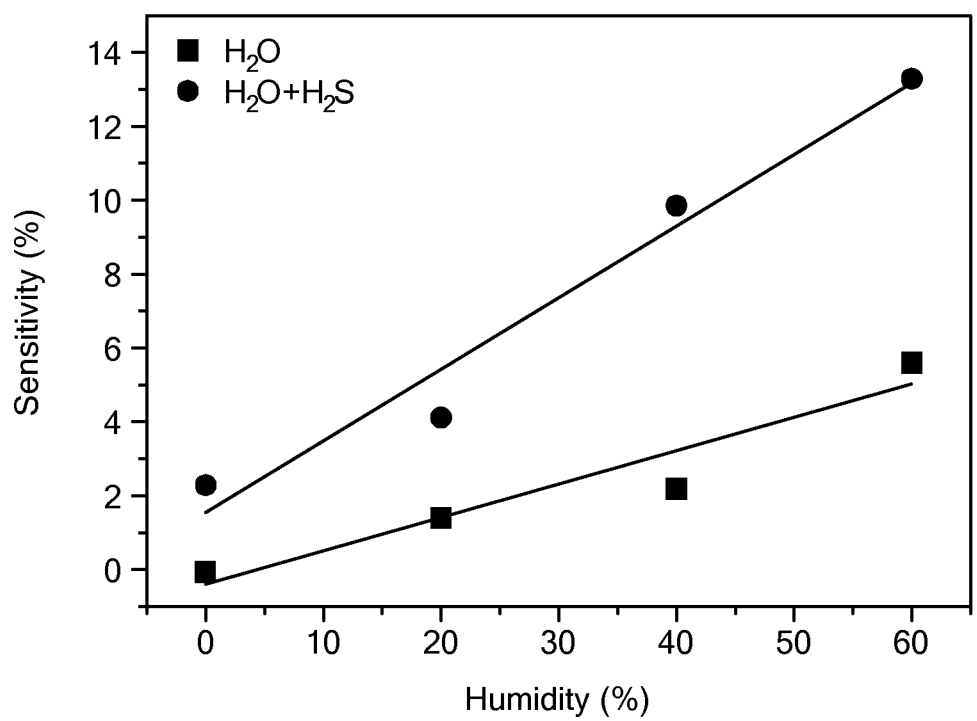

FIGS. 10A-C show the responses of a bare m-SWCNT device. FIG. 10A shows the response to water vapor. FIG. 10B shows real-time current changes during $H_2S$ detection at relative humidity of 20%, 40%, and 60%. FIG. 10C compares the sensitivity of the device to $H_2O$ or $H_2O+H_2S$ as a function of relative humidity.

Figure 11A:
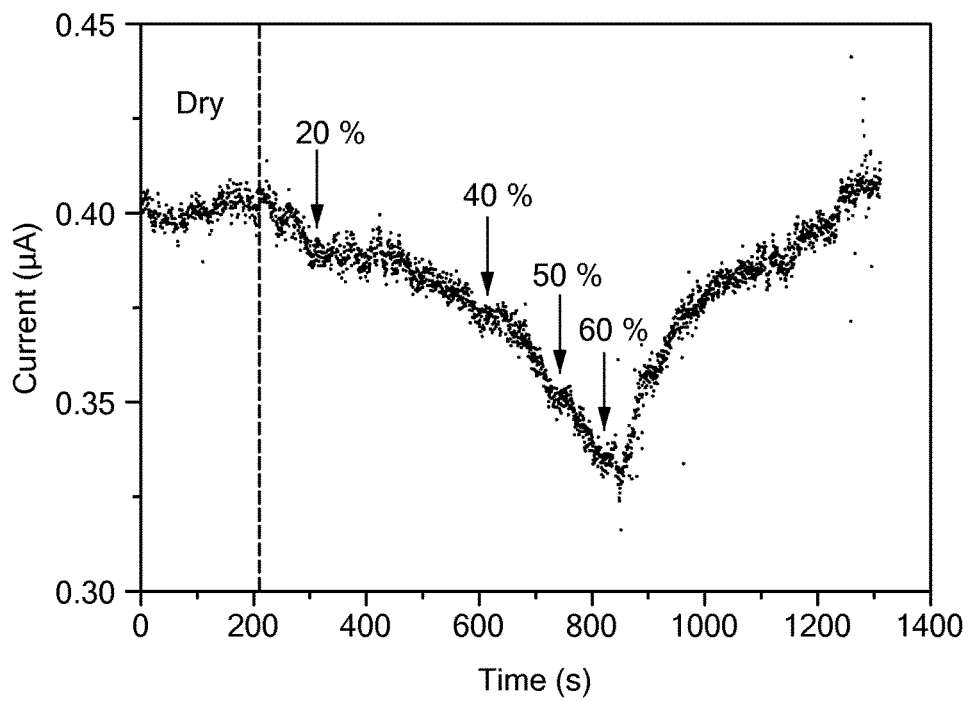
Figure 11B:
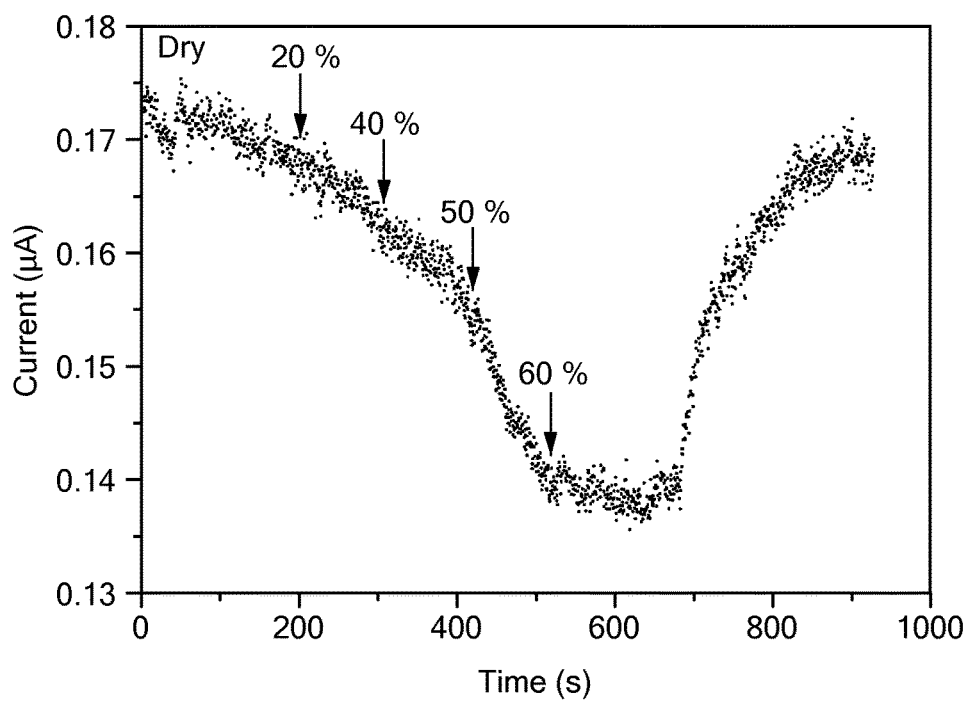
Figure 12A:
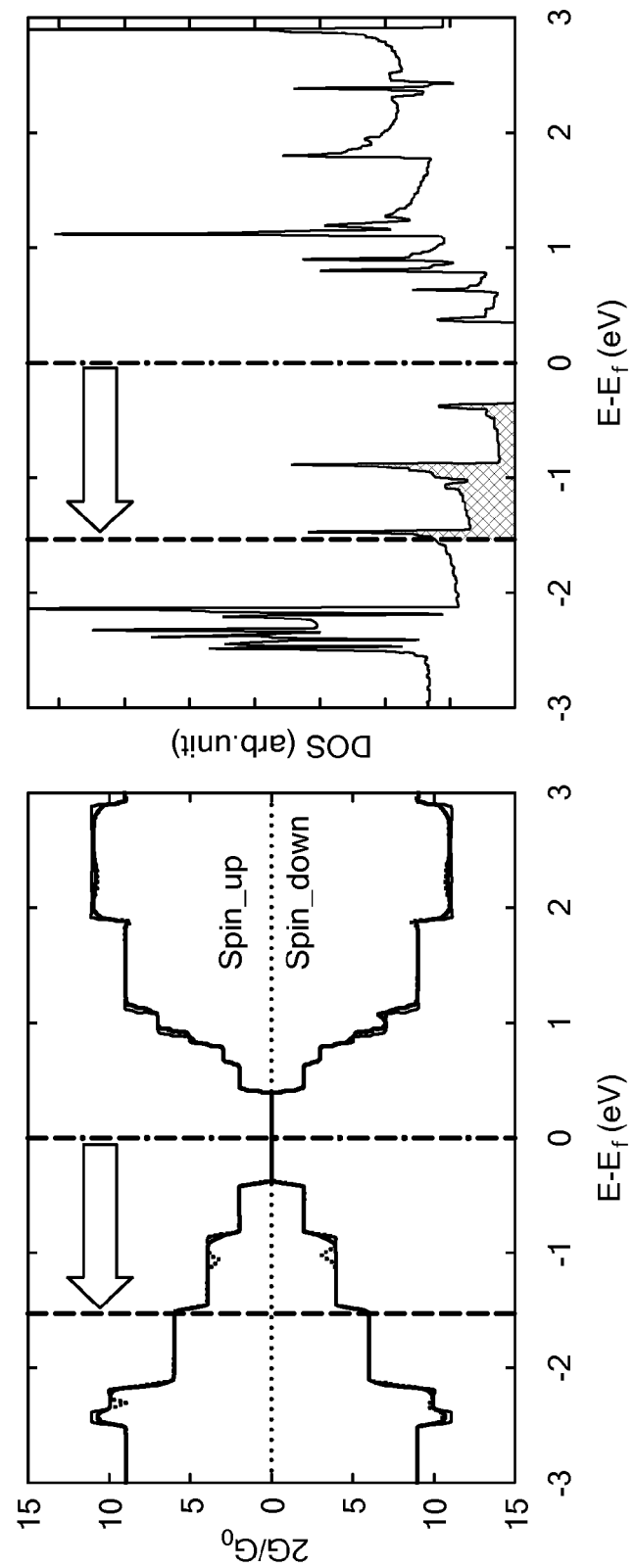
Figure 12B:
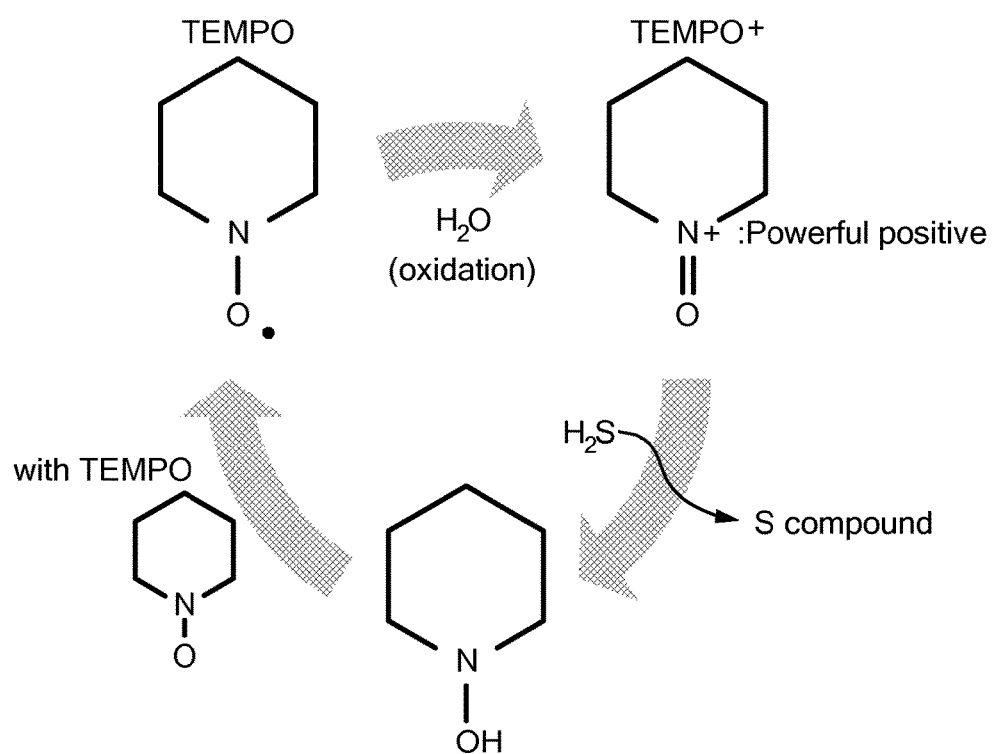

FIG. 11 shows real-time current drop of an s-SWCNT device without TEMPO (FIG. 11A) and with TEMPO (FIG. 11B) observed when only water vapor was introduced FIG. 12A shows the electronic band structure of s-SWCNT functionalized with TEMPO. FIG. 12B shows the catalytic effects of TEMPO for $H_2S$ and $H_2O$.

DETAILED DESCRIPTION OF THE INVENTION

The invention provides a carbon nanotube (CNT) or single walled carbon nanotube (SWCNT) based micron scale chemical sensor or sensor array that enables the in situ detection of chemicals both in a hydrocarbon reservoir and in a gas stream, suitable for use in very harsh environments such as those encountered during petrochemical exploration and recovery. In addition, the sensors according to the invention can serve as a platform for the development of multifunctional sensors, to perform, for example, simultaneous measurements of pressure, salinity, humidity, pH, and/or scale-forming ions (e.g. calcium, barium, magnesium, and/or strontium) on a single chip. Incorporation of read out electronics, one or more optional RF signal generator and one or more optional multiplexers into the chip enable them to communicate to a main relay station (e.g., in a subterranean reservoir), which in turn transmits the data to a receiver on the earth's surface for 3D mapping or other analysis. Implementation of simple algorithms can be used to retrieve the signal from these sensors with position and time information.

Previous SWCNT-based chemical sensors have lacked specific functionalization that allows targeted and specific detection of chemicals in air. With respect to hydrogen sulfide ($H_2S$) detection, previous SWCNT-based sensors were not specific towards hydrogen sulfide and produced too many false positives. Electrochemistry-based sensors and metallic conductance-based sensors are too large for many applications and are not sized on a microscale or nanoscale like sensors of the present invention. Predominantly these earlier sensors are designed for room temperature and pressure conditions. In contrast, the sensors of the present invention are conductance based and use microscale or nanoscale assemblies of functionalized SWCNT. Their response time is on the order of a few seconds, and they offer very high sensitivity in the ppm or ppb range. The sensors of the present invention can work in harsh environments up to temperatures of 180 C and pressures of 500 psi or even 20 Kpsi. For hydrogen sulfide detection, TEMPO (2,2,6,6-tetramethylpiperidin-1-yl)oxyl, or $(CH_2)_3(CMe_2)_2NO$) molecules can be used for functionalization, providing high selectivity and capability of detecting hydrogen sulfide in various environments. The sensors recover completely when exposed back to air and hence can be reused hundreds of thousands of times. The sensor mechanism is based on simple conductance and does not involve cumbersome electrochemical methods.

One embodiment of the sensor utilizes molecular doping of the surface of SWCNT with 2,2,6,6-tetramethylpiperidine-1-oxyl (TEMPO), where it serves as a catalyst and enables the effective detection of $H_2S$ gas by catalyzing a redox reaction at ambient temperature (e.g., room temperature). Derivatives of TEMPO that react with $H_2S$ also can be used, including 4-amino-TEMPO and 4-hydroxy-TEMPO (TEMPOL). During the sensing of $H_2S$ molecules, water vapor plays an important role in the electrical conductivity of the SWCNT of the sensor, as shown in further detail below.

Figure 1:
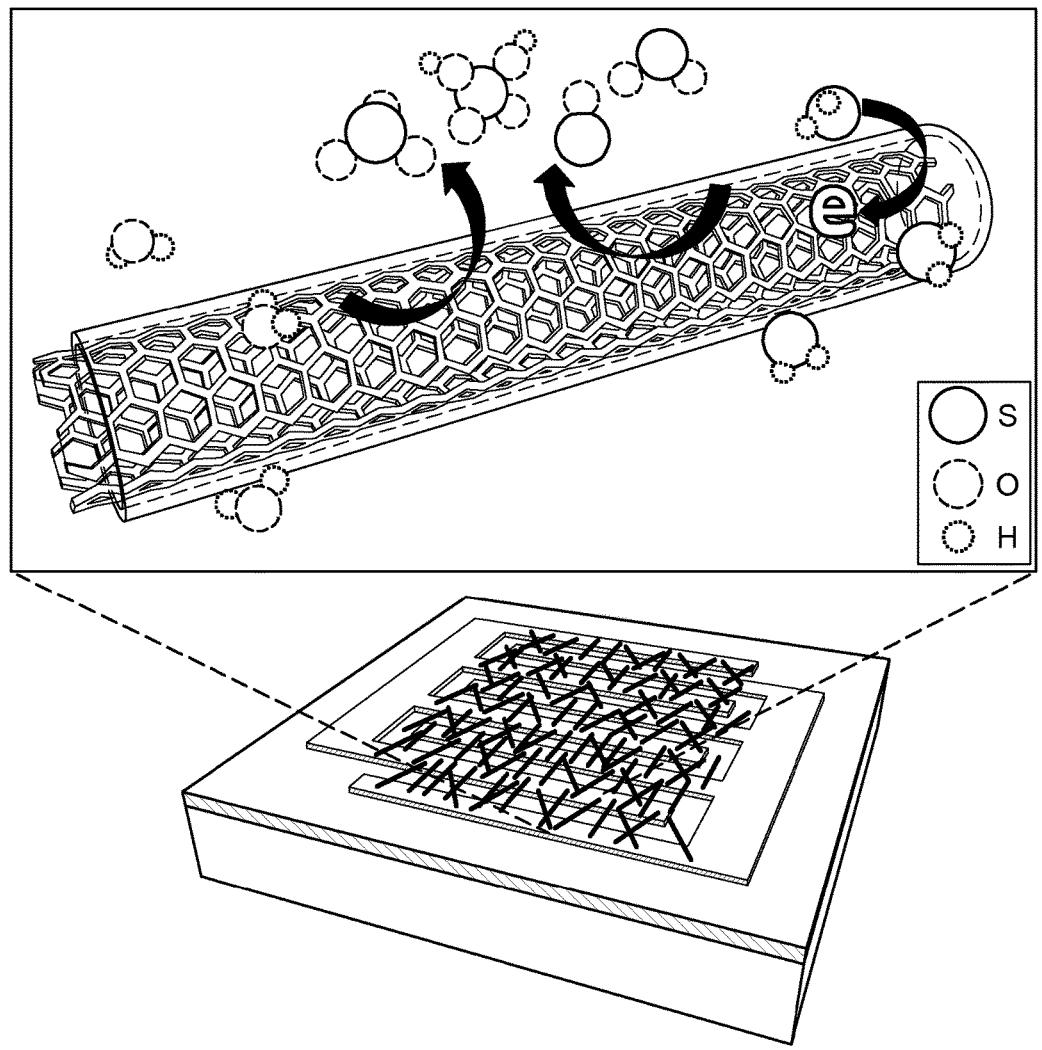
FIG. 1 shows a schematic diagram of an $H_2S$ sensor device and the chemical behavior of $H_2S$ and $H_2O$ molecules on SWCNT functionalized by TEMPO. The upper panel shows an enlarged view of a single SWCNT from the sensor, shown in the lower panel.

FIG. 1 schematically depicts a sensor device according to the invention and the behavior of $H_2S$ and $H_2O$ molecules on a SWCNT functionalized with TEMPO molecules. SWCNTs serve as an active channel layer because of their extremely high surface area to volume ratio and lack of chemical interaction with $H_2S$ or other gases that might interfere with $H_2S$ detection.

Semiconducting SWCNT (s-SWCNT) are known to be capable of undergoing redox reactions (27-28). The effect of $H_2S$ on SWCNTs with different electronic structures (semiconducting and metallic) was investigated by performing a controlled experiment in which 99% pure metallic SWCNT (m-SWCNT) or s-SWCNT solutions (purchased from NanoIntegris Inc.) were drop-casted onto each of two interdigitated finger electrodes. Then, TEMPO was deposited onto the SWCNT-based devices by vaporizing a solution of TEMPO so as to achieve a uniform and thin coating of the functionalizing agent on the SWCNTs, which were then carefully outgassed by joule heating under vacuum at $10^{-3}$ torr for 1 hr, followed by injection of dry $N_2$ gas into a controlled atmosphere chamber for recording $H_2S$ detection. TEMPO, which possesses a nitroxyl group stabilized by four adjacent methyl groups, has been used as a radical trap, as a structural probe for biological systems, as a reagent in organic synthesis, and as a mediator in controlled free radical polymerization (29-31). The present inventors have discovered that TEMPO is also capable of oxidizing gaseous $H_2S$ and can be utilized as a sensor molecule for making a chemical sensor to detect $H_2S$.

Figure 2:
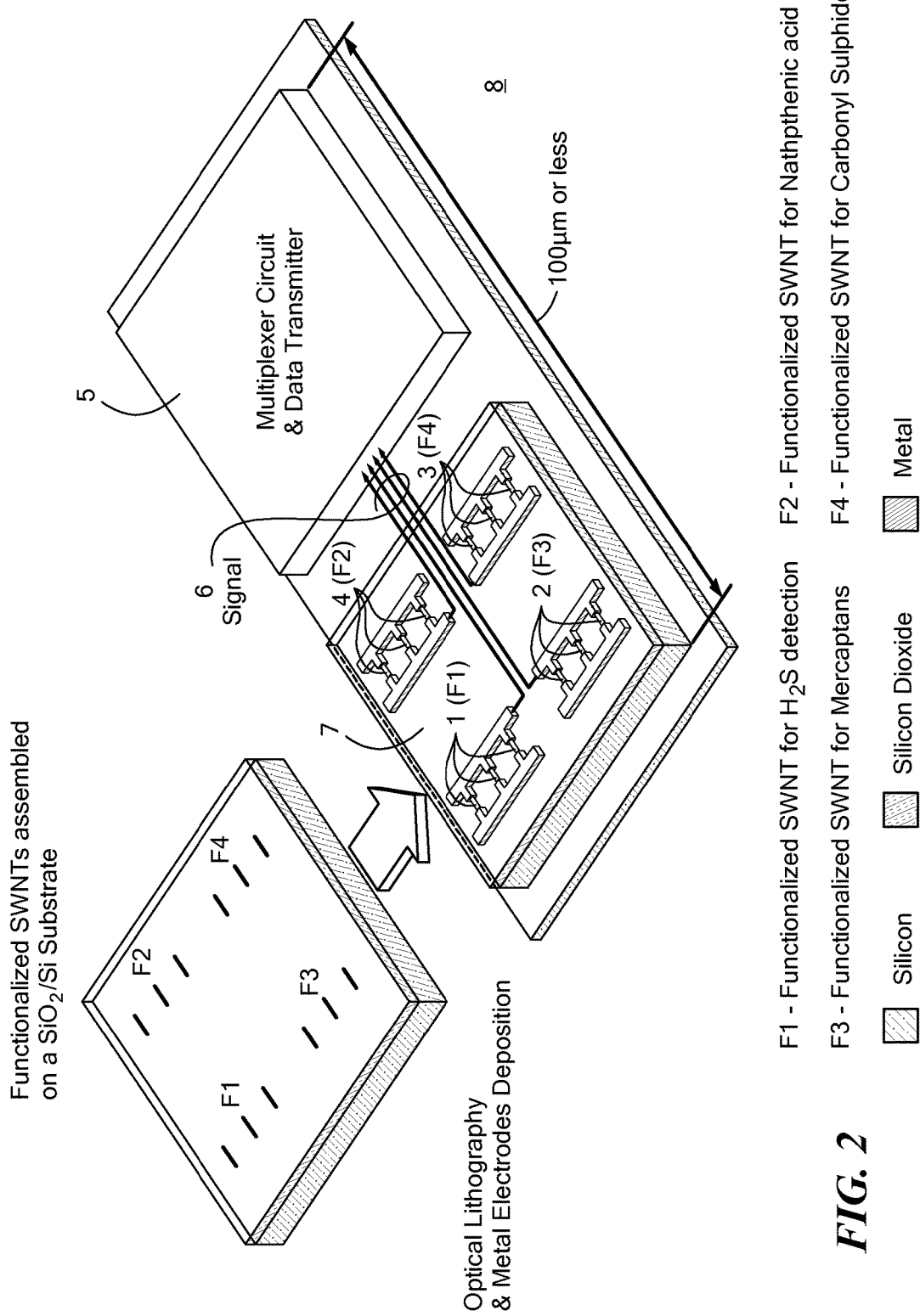
FIG. 2 shows a schematic diagram of a multiplex micronscale SWCNT based chemical sensor array.

An example of a multiplex sensor device (reference numeral 8) is shown in FIG. 2. In this example, the device contains four sensors (F1-F4, reference numerals 1-4), each designed to detect a distinct chemical analyte (e.g., $H_2S$, naphthenic acid, mercaptan, and carbonyl sulfide). In this embodiment, which is designed for remote sensing applications, the sensor chip (reference numeral 7) is electrically linked to a multiplexer circuit and data transmission chip (reference numeral 5) via one or more electrical connections (reference numeral 6). Data from the sensors are transferred to the circuit, where they can be optionally processed and subsequently transmitted to a remote receiver.

The fabrication sequence and principle of operation of a functionalized SWCNT sensor (reference numeral 70) are shown in FIG. 3. Directed assembly of SWCNTs was performed following microfabrication procedures to fabricate the devices. SWCNT can be functionalized by any suitable method for depositing the functionalizing agent (reference numeral 50) onto the SWCNT, either prior to or following assembly in the sensor. Preferably, the SWCNT are functionalized by incubating SWCNT in suspension together with a functionalizing agent (functional group) that adheres non-covalently, interacting with sidewalls of the SWCNT by means of hydrophobic interactions or pi-stacking interactions. Preferred methods of non-covalently coating the SWCNT with a functionalizing agent include drop coating, spin coating, sublimation, and evaporation or vaporization. Alternatively, the already assembled SWCNT can be functionalized by covering them with a solution containing a functionalizing agent. The base (reference numeral 10) of the sensor is an electrically insulating substrate of a material such as Si, $SiO_2$, or a combination thereof (e.g., a base of silicon coated with a layer of $SiO_2$ (reference numeral 20)). One or more pairs of electrodes (reference numeral 40) are deposited on the substrate using conventional techniques. For example, a mask layer can be applied to the substrate and patterned using lithography (e.g., photolithography, electron beam lithography, or ion beam lithography), followed by deposition of a conductive layer (e.g., a layer of gold, silver, chromium, or another electrically conductive metal, or any combination thereof) to form the electrodes, optionally with an adhesion layer deposited between the substrate and the conductive layer. A gap of insulating material (e.g., bare substrate material) is left between each pair of microelectrodes. The SWCNT are assembled into bundles that form electrical contact with the two electrodes of a pair, one electrode at each end of the bundles; the bundles of SWCNT bridge the insulating gap and provide a current path between the electrodes. Any method of assembling the nanotubes can be used. A preferred method is the fluidic assembly method which is described in Jaber-Ansari et al., J. Am. Chem. Soc. 131, 804-808 (2009) and U.S. published patent application 2010/0183844, which is hereby incorporated by reference. After assembly, the nanotube bundles (reference numeral 40) form a conductive bridge between the electrodes. In one embodiment, the SWCNT are predominantly semiconducting. SWCNT. The completed sensor device responds to interaction of the chemical agent (reference numeral 60) for which it is designed with the functional group (reference numeral 50) by altering the conductance of the SWCNT bridge (reference numeral 40).

The principle of sensor operation is conductance based. The conductance of a bundle or an array of SWCNT is modified upon the chemical interaction of a specific functional group by a chemical agent whose detection is desired. The altered conductance provides a signal that registers the presence and/or concentration of the chemical agent in the environment of the sensor. For example, SWCNTs with the non-covalently bound functional group TEMPO can serve as a conduction channel that is sensitive to hydrogen sulfide. The channel dimensions and the functional group loading values are defined by the sensitivity window provided by the functional group. The sensitivity and electrical response characteristics are also influenced by the dimensions of the channel in which the SWCNT are deposited. A preferred channel has dimensions of about 1 micron in width by about 10 microns in length, although any desired dimensions can be used. Larger channels will produce a larger conductance signal. Channels are preferably in the general form of an elongated rectangle, having a width smaller than the length, but other shapes can be used. The SWCNT deposited in a channel are in electrical contact with electrodes at both ends of the channel, and the two electrodes are electrically connected to a circuit. thus forming a two-wire circuit that can be used to measure the conductance of the SWCNT as a function of time. The interaction or exposure of these sensors to the chemical agent of interest result in a measurable change (decrease or increase) in the current flowing through the SWCNT channel, which is a signature of the presence of the chemical agent. Without intending to limit the invention in any way, it is believed that for detection of $H_2S$ by TEMPO-functionalized SWCNT, the mechanism involves a reversible redox reaction between TEMPO and $H_2S$ with involvement of carbon in the SWCNT, resulting in a reduction of the conductance of the SWCNT in the presence of $H_2S$.

By providing different functional groups, the chemical sensor of the invention can be made specific for a variety of different chemical agents. For example, using TEMPO or derivatives of TEMPO, sensors specific for $H_2S$ can be constructed. Experiments have confirmed that such sensors produce specific conductance changes (i.e., a reduction in conductance) in response to $H_2S$, while conductance was unaffected by the presence of LPG (liquified petroleum gas) and components thereof, such as the odorants thiophene and amyl mercaptans. The conductance of TEMPO-based sensors also was unaffected by nitrogen gas, water vapor, hexane, or 1-octanethiol. On the other hand, sensors made by functionalizing SWCNT with phenyl cyanide (also known as benzonitrile and cyanobenzene) show conductance changes in the presence of mercaptans.

A photographic image of a finished device with wire bonding is presented in FIG. 4. The response times of this sensor device for various concentrations of $H_2S$ under various conditions are shown in FIG. 5, which demonstrates the selectivity, specificity and versatility of the sensor.

The effect of the TEMPO molecule concentration on SWCNT was studied by adjusting the concentration of TEMPO in the solution that was drop casted onto the SWCNT. In FIG. 6A a top-viewed high resolution SEM image of the SWCNT channel with loading of TEMPO is shown (e.g., in the micromolar range), while in FIG. 6B, an SWCNT channel is shown for which 100 times greater TEMPO loading was used than in FIG. 6A. It can be clearly seen from FIGS. 6A and 6B that the higher TEMPO concentration increased the coverage of the channel by SWCNT. Sensor testing was carried out to determine the sensitivity for $H_2S$ detection as a function of the TEMPO concentration. FIG. 6C is a plot of the response time of the sensor as a function of the concentration of $H_2S$ gas in atmospheric air. The "response time" is defined as the time period the sensor took to increase its initial resistance (virgin state in the absence of any $H_2S$) by a value of 10%. As can be observed, the sensor response time is on the order of minutes for lower concentrations of $H_2S$, while it reached a saturation value above 250 ppm of $H_2S$. The saturation in the response time is an indication that all of the TEMPO molecules have interacted with the $H_2S$. The inset in FIG. 6C shows the response time for less than 100 ppm $H_2S$ detection, corresponding to the concentration of the TEMPO molecule on the SWCNT channel shown in FIGS. 6A and 6B respectively. When the concentration of the TEMPO molecules was increased by two orders of magnitude, the response time of the sensor, for very low concentrations of $H_2S$, decreased by an order magnitude. This indicates that the TEMPO molecule-$H_2S$ interaction is the primary contributor to the conductance change rather than the SWCNT-$H_2S$ interaction. Thus, the concentration of the functional group plays a key role in the detection range and response time.

The recovery of the device when exposed to atmospheric air is shown in FIG. 7. As can be seen from the graph, recovery is rapid and complete within seconds to minutes, with no visible loss of sensitivity or drift in baseline conductance after several cycles.

In certain embodiments the sensor is a multiplex sensor, having two or more sections each devoted to detection of a different chemical agent or class of chemical agents. The multiplex sensor embodiment utilizes a differently functionalized SWCNT set to detect each corresponding chemical agent. In one embodiment, the multiplex sensor can include one or more sensors for humidity, pH, oxygen, salt concentration, or other conditions that can affect one or more chemical sensors on the device, for use in calibrating the responses of the other sensors. The multiplex sensor can be configured so as to contain two or more sections, each of which detects a different chemical agent, because each section contains a set of distinctly functionalized SWCNT and is connected to a different set of circuitry. In order to fabricate such a multiplex sensor, each section can be fabricated in a separate process, and the complete set of sensor sections can be fabricated sequentially. For example, a first sensor section, capable of detecting $agent_1$, can be fabricated by performing lithography on the substrate to prepare a set of channels for $SWCNT_1$ deposition, and functionalized $SWCNT_1$ are deposited in those channels. Alternatively, non-functionalized SWCNT can be deposited and then functionalized in situ to create $SWCNT_1$ by adding one or more reagents to the deposited SWCNT so as to add functional group1 to the SWCNT. Subsequently, a second sensor section, capable of detecting agent2, can be added to the sensor to form a multiplex sensor. A second set of channels is then added to the sensor by photolithography, which is performed in a manner that does not disturb the already formed first sensor. $SWCNT_2$ are then added to the second set of channels as before, adding the capability to detect $agent_2$ simultaneously with detection of $agent_1$. Fabrication can continue in this manner to add as many sensor sections as desired. For example, 2, 3, 4, 6, 8, 9, 10, 12, 15, 20, or more separate sensor sections can be added to the multiplex sensor.

In order to test a sensor according to the present invention, non-covalently functionalized SWCNT devices were exposed to $H_2S$ gas under either dry $N_2$ or controlled water vapor conditions. In an $H_2S$ detection process according to the invention, the sensing materials can come in contact with either $H_2O$ or $H_2S$ or mixtures of these two.

FIGS. 8A-8D show the sensing of $H_2S$ molecules with various SWCNT devices of the invention, and the effect of relative humidity (RH). In order to investigate the sensing mechanism and the interactions between SWCNT-TEMPO and $H_2S$ or $H_2O$, sensor performance was compared for sensors constructed using s-SWCNT and m-SWCNT both with and without TEMPO, and in the presence of water molecules. First, to investigate the effects of $H_2S$ gas on bare SWCNT, nanotube sensor devices without TEMPO functionalization were exposed to $H_2S$ gas at 5, 10, 50, 100, and 200 ppm in the chamber in an atmosphere of dry $N_2$. Sensitivities were compared at each concentration of $H_2S$ gas using the value $S=(\{(R_{gas}-R_i))/(R_i\}\times100)$, where $R_i$ is the initial resistance in dry $N_2$ and $R_{gas}$ is the changed resistance after injection of $H_2S$ gas. FIG. 8A shows the sensitivity of a bare s-SWCNT device in dry $N_2$ (see FIG. 9A for real time current change). The change in resistance value is a linear function of $H_2S$ concentration, with a linear slope of 0.27 per ppm, showing 40% change in sensitivity at $H_2S$ concentrations as high as 200 ppm. However, a bare m-SWCNT device showed less than 5% sensitivity (see FIG. 9B) in detecting $H_2S$ gas. This result indicates much greater redox properties of s-SWCNT compared with m-SWCNT.

The effect of $H_2O$ on sensing of $H_2S$ was measured at 100 ppm $H_2S$, which is the minimum concentration at which the olfactory nerve can be paralyzed after a few inhalations. Thus, the sensing of 100 ppm $H_2S$ was tested at different RH values. FIG. 8B shows the real-time current changes in a bare s-SWCNT device when the sensor was exposed to 100 ppm $H_2S$ gas at RH of 0, 20%, 40%, and 60% (see FIG. 10A-10C for bare m-SWCNT device, showing sensing of water vapor (FIG. 10A), real-time current changes in $H_2S$ at 0, 20%, 40%, and 60% RH (FIG. 10B), and comparison of sensitivity as a function of RH). First, the current in the s-SWCNT device decreased when it was exposed to water vapor. Then, a further substantial decrease in conductance was observed when 100 ppm $H_2S$ gas was introduced at the predetermined RH levels. Once the current saturated, the chamber was exposed to dry $N_2$ to allow sensor recovery and sensing of $H_2S$ at higher RH. The real-time current measurements clearly demonstrate that redox properties do change in the presence of $H_2S$ and water vapor. The sensitivity of bare s-SWCNT devices was increased significantly to 150% at 60% RH (FIG. 8B).

$H_2O$ molecules can be adsorbed onto the surface of SWCNTs where they act as electron donors in a p-type semiconductor, reducing the hole density in s-SWCNT and decreasing the current (25). This is consistent with the initial current drop observed when only water vapor was introduced as shown in FIG. 8B and FIG. 11B. The interaction of $H_2S$ and $H_2O$ molecules could explain the increased $H_2S$ sensitivity of s-SWCNT at higher humidity. $H_2S$ is slightly soluble in water (its solubility is about 3.8 g per kg in water) and acts as a weak acid. The $H_2O$ concentration at 60% RH and 20° C. is about 38000 ppm, which is enough to dissolve 100 ppm of $H_2S$. Therefore, the conductance after injection of $H_2S$ gas can be changed significantly by hydrosulfuric acid formed by water molecules attached on the surface of s-SWCNTs. This demonstrates that moisture is an important factor governing the practical application and sensitivity of the chemical sensors of the invention.

In order to maximize sensitivity of the $H_2S$ sensor in view of the effect of $H_2O$ as shown above, TEMPO was used as a homogeneous catalyst for redox reaction of $H_2S$ and $H_2O$. As shown in FIGS. 8C and 8D, s-SWCNT devices functionalized with TEMPO showed 420% sensitivity at 60% RH, which is about 3 times higher than a bare s-SWCNT sensor, and 17 times higher than bare s-SWCNT device used in dry $N_2$.

The sensor response based on TEMPO-functionalized s-SWCNT is dependent both on the electronic properties of the SWCNT as the active channel and on the catalytic effects and functionalization of TEMPO. Without intending to limit the invention to any particular mechanism, the inventors expect that the electronic structures, and consequently the transport properties of SWCNT, are susceptible to influence by the presence of adsorbates due to the fact that every atom in a SWCNT can be considered a surface atom and is exposed to the environment. For the relationship between s-SWCNT and TEMPO, FIG. 12A shows the electronic band structure of SWCNTs for spin-up and spin-down electrons using a local density approximation (LDA). The spin polarization is mostly derived from TEMPO molecules. With the very small binding energy obtained in these calculations, the sum of all interactions can best be considered as a physical adsorption. Typically, the C—C bonds of physisorbed SWCNT are not stretched or quenched in the physical sense. The weak binding of TEMPO on SWCNT surface preserves the characteristic conical u bands touching at the k/k' points (32). This means that holes are donated by the TEMPO molecules to the SWCNT, which becomes p-type doped. A very small hole doping is observed in the band structure. The doping level and polarity are very sensitive to adsorption distance.

A reaction mechanism for the interaction of $H_2O$ and $H_2S$ with TEMPO-functionalized SWCNT is shown in FIG. 12B. An $H_2O$ molecule first adsorbs onto the surface of a TEMPO-functionalized SWCNT and then dissociates, oxidizing TEMPO to TEMPO$^+$ with a positive charge. After this, an $H_2S$ molecule dissociates via catalysis by TEMPO$^+$, losing first one hydrogen atom and then a second one. The sulfur left on the surface generates sulfur oxides as well as $H_2O$ by combining with $O_2$ from $O_2^-$ adsorbed on the SWCNT, resulting in back donation of electrons to the SWCNT, which becomes less p-doped. Such electron backdonation to SWCNT can reduce the conductance in the presence of $H_2S$. The presence of $H_2O$ is believed to enhance the catalytic effect of TEMPO and thus lead to a larger conductance change than in the dry condition.

REFERENCES (1) Peng, H.; Cheng, Y.; Dai, C.; King, A. L.; Predmore, B. L.; Lefer, D.; Wang, B. Angew. Chem. Int. Ed. 2011, 50, 9672.
(2) Abe, K.; Kimura, H. J. Neurosci. 1996, 16, 1066.
(3) Wesenberg, G.; Proctor, N. H. Chemical Hazards of the workplace, 4th edition, Wiley, New York, 1996.
(4) Yang, B.; Wang, S.; Tian, S.; Liu, L. Electrochem. Commun. 2009, 11, 1230.
(5) Chen, Si.; Chen, Z.; Ren, W.; Ai, H. J. Am. Chem. Soc. 2012, 134, 9589.
(6) Wu, X.; Kercher, A. K.; Schwartz, V.; Overbury, S. H.; Armstrong, T. R. Carbon 2005, 43, 1084.
(7) Dzhafarov, T. D.; Yuksel, S. A. J. Nanosci. Nanotechnol. 2011, 11, 9012.
(8) Schiavon, G.; Zotti, G.; Toniolo, R.; Bontempelli, G. Anal. Chem. 1995, 67, 318.
(9) Mubeen, S.; Zhang, T.; Chartuprayoon, N.; Rheem, Y.; Mulchandani, A.; Myung, N.; Deshusses, M. Anal. Chem. 2010, 82, 250.
(10) Comini, E. Anal. Chim. Acta 2006, 568, 28.
(11) Sun, Z.; Yuan, H.; Liu, Z.; Han, B.; Zhang, X. Adv. Mater. 2005, 17, 2993.
(12) Chowdhuri, A.; Gupta, V., Sreenivas, K.; Kumar, R.; Mozumdar, S.; Patanjali, P. K. Appl. Phys. Lett. 2004, 84, 1180.
(13) Strano, M. S.; Dyke, C. A.; Usrey, M. L.; Barone, P. W.; Allen, M. J.; Shan, H.; Kittrell, C.; Hauge, R. H.; Tour, J. M.; Smalley, R. E. Science 2003, 301, 1519.
(14) Snow, E. S.; Perkins, F. K.; Houser, E. J.; Badescu, S. C.; Reinecke, T. L. Science 2005, 307, 1942.
(15) Kong, J.; Franklin, N. R.; Zhou, C. W.; Chapline, M. G.; Peng, S.; Cho, K. J.; Dai, H. Science 2000, 287, 622
(16) Lu, Y.; Meyyappan, M.; Li, J. Small 2011, 7, 1714.
(17) Tang, X.; Bansaruntip, S.; Nakayama, N.; Yenilmez, E.; Chang, Y.; Wang, Q. Nano Lett. 2006, 6, 1632.
(18) Kawano, T.; Chiamori, H. C.; Suter, M.; Zhou, Q.; Sosnowchik, B. D.; Lin, L. Nano Lett. 2007, 7, 3686.
(19) Kauffman, D. R.; Star, A. Angew. Chem. Int. Ed. 2008, 47, 6550.
(20) McAlpine, M. C.; Ahmad, H.; Wang, D.; Heath, J. R.; Nat. Mater. 2007, 6. 379.
(21) Shirsat, M. D.; Sarkar, T.; Kakoullis, J.; Myung, N. V.; Konnanath, B.; Spanias, A.; Mulchandani, A. J. Phys. Chem. C 2012, 116, 3845.
(22) Kumar, M. K.; Ramaprabhu, S. J. Phys. Chem. B 2006, 110, 11291.
(23) Zanoll, Z.; Leghrib, R.; Felten, A.; Pireaux, J.; Llobet, E.; Charlier, J. ACS Nano 2011, 5, 4592.
(24) Star, A.; Joshi, V.; Skarupo, S.; Thomas, D.; Gabriel, J. P. J. Phys. Chem. B 2006, 110, 21014.
(25) Zahab, A.; Spina, N.; Poncharal, P.; Phys. Rev. B 2000, 62, 10000.
(26) Cappelletti, D.; Ronca, E.; Belpassi, L.; Tarantelli, F.; Pirani, F. Acc. Chem. Res. 2012, ASAP.
(27) Balasubramanian, K.; Burghard, M. J. Mater. Chem. 2008, 18, 3071.
(28) Ming, Z.; Diner, B. A. J. Am. Chem. Soc. 2004, 126, 15490.
(29) Jeena, V.; Robinson, R. S. Chem. Commun. 2012, 48, 299.
(30) Saito, T.; Nishiyama, Y.; Putaux, J.; Vignon, M.; lsogai, A. Biom-acromolecules 2006, 7, 1687.
(31) Jing, Y.; Jiang, J.; Yan, B.; Lu, S.; Jiao, J.; Xue, H.; Yang, G.; Zheng, G. Adv. Synth. Catal. 2011, 353, 1146.
(32) Slawinska, J.; Dabrowski, P.; Zasada, I. Phys. Rev. B 2011, 83, 245429.

The invention claimed is:

1. A microscale sensor for detecting a chemical agent, the sensor comprising:
    a substrate;
    a conductive layer attached to a surface of the substrate, the conductive layer forming at least one pair of electrodes with an insulating gap between the electrodes; and
    a conductive bridge consisting essentially of one or more functionalized single-walled carbon nanotubes bridging the gap between the electrodes;
wherein the one or more nanotubes are functionalized with a functional group that reacts with said chemical agent, whereby the conductivity of the conductive bridge is modified; and
wherein the functional group is TEMPO (2,2,6,6-tetramethylpiperidin-1-yl)oxy) or a TEMPO derivative and the chemical agent is hydrogen sulfide, or wherein the functional group is phenyl cyanide and the chemical agent is a mercaptan.

2. The sensor of claim 1, wherein the single-walled carbon nanotubes are semiconducting.

3. The sensor of claim 1, further comprising a microelectronic circuit for receiving and/or processing of an electrical signal from said electrodes.

4. The sensor of claim 1, further comprising a transmitter for sending data obtained by the sensor to a remote receiver.

5. The sensor of claim 1, comprising a plurality of conductive bridges of one or more functionalized single-walled carbon nanotubes, each bridging a gap between said electrodes.

6. The sensor of claim 5, wherein the plurality of bridges forms a two-dimensional array of single-walled carbon nanotubes.

7. The sensor of claim 1 which is a multiplex sensor capable of detecting two or more different chemical agents.

8. The sensor of claim 1 which specifically detects hydrogen sulfide and wherein the functional group is TEMPO (2,2,6,6-tetramethylpiperidin-1-yl)oxyl) or a TEMPO derivative.

9. The sensor of claim 8, wherein the wherein the functional group is TEMPO derivative, and the TEMPO derivative is 4-amino TEMPO or 4-hydroxy TEMPO.

10. The sensor of claim 1 which detects said chemical agent at temperatures up to 180° C.

11. The sensor of claim 1 which detects said chemical agent at pressures up to 20 kpsi.

12. A method of detecting a chemical agent in a sample, the method comprising the steps of:
(a) providing the microscale sensor of claim 1;
(b) measuring a baseline conductance value of the conductive bridge of the sensor in the absence of the sample;
(c) exposing the conductive bridge to the sample; and
(d) measuring a change in the conductance of the bridge in the presence of the sample compared to the absence of the sample, wherein the change in conductance indicates the presence or absence of the chemical agent in the sample;
wherein the chemical agent is hydrogen sulfide or a mercaptan.

13. The method of claim 12, wherein the amount or concentration of the chemical agent in the sample is determined by comparing the change in conductance value to a calibration for said chemical agent.

14. The method of claim 12, wherein the sample is a gas.

15. The method of claim 14, wherein the relative humidity of the gas is controlled by adding water vapor to the gas or removing water vapor from the gas prior to exposing the conductive bridge to the gas.

16. The method of claim 12, wherein two or more chemical agents are detected simultaneously.

17. The method of claim 12, wherein conductance data from the sensor are processed in a data processor integrated into the sensor device.

18. The method of claim 12 wherein conductance data from the sensor are transmitted to a remote receiver.

19. The method of claim 17, wherein processed data from the data processor are transmitted to a remote receiver.

20. The method of claim 18, wherein data are transmitted from a plurality of sensors and a map of the presence or concentration of the chemical agent is produced.

21. The method of claim 19, wherein data are transmitted from a plurality of sensors and a map of the presence or concentration of the chemical agent is produced.

* * * * *